United States Patent
Glück et al.

(10) Patent No.: US 7,829,324 B2
(45) Date of Patent: Nov. 9, 2010

(54) METHOD FOR THE MICROBIOLOGICAL ISOMERISATION OF ALPHA-HYDROXY CARBOXYLIC ACIDS

(75) Inventors: Silvia Glück, Graz (AT); Barbara Schnell, Graz (AT); Monika Pirker, Graz (AT); Kurt Faber, Graz (AT)

(73) Assignee: BASF SE, Ludwigshafen (DE)

( * ) Notice: Subject to any disclaimer, the term of this patent is extended or adjusted under 35 U.S.C. 154(b) by 457 days.

(21) Appl. No.: 10/560,455

(22) PCT Filed: Jun. 17, 2004

(86) PCT No.: PCT/EP2004/006564

§ 371 (c)(1),
(2), (4) Date: Dec. 14, 2005

(87) PCT Pub. No.: WO2004/111257

PCT Pub. Date: Dec. 23, 2004

(65) Prior Publication Data

US 2006/0148051 A1    Jul. 6, 2006

(30) Foreign Application Priority Data

Jun. 18, 2003    (DE) .............................. 103 27 582

(51) Int. Cl.
*C12P 7/40*    (2006.01)
(52) U.S. Cl. ..................... 435/280; 435/252.9; 435/136
(58) Field of Classification Search ....................... None
See application file for complete search history.

(56) References Cited

U.S. PATENT DOCUMENTS 5,534,436 A * 7/1996 Seufer-Wasserthal et al. .... 435/280
6,605,430 B1 * 8/2003 Affholter et al. ............... 506/5

FOREIGN PATENT DOCUMENTS

EP    0596466    5/1994

OTHER PUBLICATIONS

Dennis et al., Annals of the New York Academy of Sciences, Jul. 1965, vol. 119, No. 3 : pp. 868-876.*
Hiyama et al. , J Biochem.1968; 64: 99-107.*
Stetter et al., Arch Mikrobiol. Dec. 31, 1973;94(3):221-47.*
DSMZ Catalogue on line, accessed Jun. 26, 2008 (1 page)—http://www.dsmz.de/microorganisms/html/strains/strain.dsm020017.html.*
DSMZ Catalogue on line, accessed Jun. 26, 2008 (1 page)—http://www.dsmz.de/microorganisms/html/strains/strain.dsm020207.html.*
Glueck, S. M., et al., "Lactate Racemase As a Versatile Tool for the Racemization of α-Hydroxycarboxylic Acids", Chem. Listy, 2003, vol. 97, p. 431.
Schnell, B., et al., "Enzymatic Racemisation and its Application to Synthetic Biotransformations", Advanced Synthesis & Catalysis, 2003, vol. 345, pp. 653-666.
Liu, S-Q., "Practical Implications of Lactate and Pyruvate Metabolism by Lactic Acid Bacteria in Food and Beverage Fermentations", International Journal of Food Microbiology, 2003, vol. 83, pp. 115-131.
Strauss. U.T., et al., "Deracemization of (±)-Mandelic Acid Using a Lipase-Mandelate Racemase Two-enzyme System", Tetrahedron: *Asymmetry*, 1999, vol. 10, pp. 4079-4081.
Felfer, U., et al., "Substrate Spectrum of Mandelate Racemase Part 2. (Hetero)-Aryl-Substituted Mandelate Derivatives and Modulation of Activity", Journal of Molecular Catalysis B: Enzymatic, 2001, vol. 15, pp. 213-222.
Schafer, S.L., et al., "Mechanism of the Reaction Catalyzed by Mandelate Racemase: Structure and Mechanistic Properties of the D270N Mutant", Biochemistry, 1996, vol. 35, pp. 5662-5669.
Garcia-Viloca, M., et al., "A QM/MM Study of the Racemization of Vinylglycolate Catalyzed by Mandelate Racemase Enzyme", Journal of the American Chemical Society, 2001, vol. 123, pp. 709-721.
Li, R., et al., "Racemization of Vinylglycolate Catalyzed by Mandelate Racemase", Journal of Organic Chemistry, 1995, vol. 60, pp. 3347-3351.
Kenyon, G.L., et al., "Mandelate Racemase: Structure—Function Studies of a Pseudosymmetric Enzyme", Acc. Chem. Res., 1995, vol. 28, pp. 178-186.
Pearson, W.R., et al., "Improved Tools for Biological Sequence Comparison", Proc. Natl. Acad. Sci. USA, 1988, vol. 85, pp. 2444-2448.
Narang, S.A., "DNA Synthesis", *Tetrahedron*, 1983, vol. 39, No. 1, pp. 3-22.
Itakura, K., et al., "Synthesis and Use of Synthetic Oligonucleotides", Ann. Rev. Biochem., 1984, vol. 53, pp. 323-356.
Itakura, K., et al., Expression in *Escherichia coli* of a Chemically Synthesized Gene for the Hormone Somatostatin, 1977, vol. 198, pp. 1056-1063.
Ike, Y., et al., "Solid Phase Synthesis of Polynucleotides. VIII. Synthesis of Mixed Oligodeoxyribonucleotides by the Phosphotriester Solid Phase Method", Nucleic Acids Research, 1983, vol. 11, No. 2, pp. 477-488.
Arkin, A.P., et al., "An Algorithm for Protein Engineering: Simulations of Recursive Ensemble Mutagenesis", Proc. Natl. Acad. Sci. USA, 1992, vol. 89, pp. 7811-7815.

(Continued)

*Primary Examiner*—Irene Marx
(74) *Attorney, Agent, or Firm*—Connolly Bove Lodge & Hutz, LLP

(57) ABSTRACT

The present invention relates to a method for the microbiological isomerization of alpha-hydroxycarboxylic acids using an alpha-hydroxycarboxylic acid racemase, the enzymes used for this method and microorganisms which express a suitable racemase activity, a screening method for microorganisms with alpha-hydroxycarboxylic acid racemase activity, the nucleic acid sequences encoding this enzyme, expression vectors, recombinant microorganisms which express this racemase, and methods for the production or isolation of a protein with alpha-hydroxycarboxylic acid racemase activity.

10 Claims, No Drawings

OTHER PUBLICATIONS

Delagrave, S., et al., "Recursive Ensemble Mutagenesis", *Protein Engineering*, 1993, vol. 6, No. 3, pp. 327-331.

Thomas, K.R., et al., "Site-Directed Mutagenesis by Gene Targeting in Mouse Embryo-Derived Stem Cells", *Cell*, 1987, vol. 51, pp. 503-512.

Ebbers, E.J., et al., "Controlled Racemization of Optically Active Organic Compounds: Prospects for Asymmetric Transformation", *Tetrahedron*, 1997, vol. 53, No. 28, pp. 9417-9476.

van Rantwijk, F., et al., "Lipase-Catalyzed Synthesis of Carboxylic Amides: Nitrogen Nucleophiles as Acyl Acceptor", *Monatshefte für Chemie*, 2000, vol. 131, pp. 549-569.

Stockland, A. E., et al., "Multiple Forms of Lactate Dehydrogenase in *Staphylococcus aureus*", Journal of Bacteriology, 1969, vol. 100, No. 1, pp. 347-353.

Hino, T., et al,, "Presence of Lactate Dehydrogenase and Lactate Racemase in *Megasphaera elsdenii* Grown on Glucose or Lactate", Applied and Environmental Microbiology, 1993, vol. 58, No. 1, pp. 255-259.

Pepple, J. S., et al., "Lactate Racemase: Hydroxylamine-Dependent $^{18}$O Exchange of the α-Hydroxyl of Lactic Acid", Biochimica et Biophysica Acta, 1976, vol. 429, pp. 1036-1040.

* cited by examiner

METHOD FOR THE MICROBIOLOGICAL ISOMERISATION OF ALPHA-HYDROXY CARBOXYLIC ACIDS

RELATED APPLICATIONS

This application is a national stage application (under 35 U.S.C. 371) of PCT/EP2004/006564 filed Jun. 17, 2004 which claims benefit to German application 103 27 582.7 filed Jun. 18, 2003.

The present invention relates to a method for the microbiological isomerization of alpha-hydroxycarboxylic acids using an alpha-hydroxycarboxylic acid racemase, the enzymes used for this method and microorganisms which express a suitable racemase activity, a screening method for microorganisms with alpha-hydroxycarboxylic acid racemase activity, the nucleic acid sequences encoding this enzyme, expression vectors, recombinant microorganisms which express this racemase, and methods for the production or isolation of a protein with alpha-hydroxycarboxylic acid racemase activity.

BACKGROUND OF THE INVENTION

The prior art knows what are known as microbial mandelate racemases, which are capable of racemizing mandelic acid in vitro or in vivo (G. L. Kenyon, J. A. Gerlt, G. A. Petsko and J. W. Kozarich, "Mandelate Racemase: Structure-Function Studies of a Pseudosymmetric Enzyme", Accts. Chem. Res., 28, 178-186 (1995); R. Li, V. M. Powers, J. W. Kozarich and G. L. Kenyon, "Racemization of Vinylglycolate Catalyzed by Mandelate Racemase", J. Org. Chem., 60, 3347-3351 (1995); S. S. Schafer, A. T. Kallarakal, J. W. Kozarich, J. A. Gerlt, J. R. Clifton and G. L. Kenyon, "Mechanism of the Reaction Catalyzed by Mandelate Racemase: The Structure and Mechanistic Properties of the D270N Mutant", Biochemistry, 35, 5662-5669 (1996)).

At the same time, the simple production of chiral, nonracemic substances, for example for the production of active ingredients in the pharmaceuticals industry, is greatly needed. The enzyme-catalyzed racemization of a stereoisomeric form of a compound, which leads to the desired enantiomer, would constitute a suitable route for producing the desired, chiral, nonracemic materials. However, the racemases known to date are distinguished by their high substrate specificity. Thus, mandelate racemase is only suitable for the biocatalytic racemization of beta,gamma-unsaturated alpha-hydroxyacids. Saturated alpha-hydroxycarboxylic acids are not accepted (cf. Felfer, U. et al., J. Mol. Catal. B: Enzymatic 15, 213 (2001)).

SUMMARY OF THE INVENTION

Enzymes with racemase activity which have a different, or widened, substrate spectrum in comparison with known racemases are therefore required.

It is an object of the present invention to provide microorganisms and enzyme preparations with a novel racemase activity, and to provide methods for the racemization of stereoisomeric chemical compounds using these enzymes or microorganisms.

Surprisingly, we have found that this object is achieved by a method for the microbiological isomerization of alpha-hydroxycarboxylic acids using an enzyme with alpha-hydroxycarboxylic racemase activity.

A first aspect of the invention relates to a method for the microbiological isomerization of alpha-hydroxycarboxylic acids of the formula I

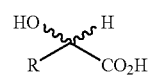

where

R is straight-chain or branched lower alkyl or lower alkenyl, preferably $C_2$-$C_8$ alkyl, or —$(CH_2)_n$-Cyc, where n is an integer of 0 to 4, preferably 1, 2 or 3, and Cyc is an unsubstituted or mono- or polysubstituted, mono- or binuclear carbo- or heterocyclic ring such as, for example, an unsubstituted or substituted aromatic or heteroaromatic ring, preferably an unsubstituted or substituted mononuclear aromatic ring, where a substrate comprising essentially a first stereoisomeric form ((R) or (S) form) of an alpha-hydroxycarboxylic acid of the formula (I) is isomerized with the aid of an enzyme with alpha-hydroxycarboxylic acid racemase activity and, if appropriate, the resulting isomer mixture ((R)/(S)) or a resulting second stereoisomer ((S) or (R) form) is isolated, or a resulting second stereoisomer is removed from the reaction equilibrium.

The enzymatic isomerization is preferably carried out by reacting the substrate with purified enzyme, for example with a degree of purity of >50%, such as, for example, >80% or >90%, or 90 to 99% on protein basis, an enzyme-containing cell extract (for example crude extract following cell disruption and removal of cell debris) or in the presence of intact cells which express at least one enzyme with alpha-hydroxycarboxylic racemase activity.

The enzyme with alpha-hydroxycarboxylic acid racemase activity can preferably be isolated from microorganisms which form or metabolize lactate, such as, for example, lactic acid bacteria or propionic acid bacteria. Particularly suitable sources are bacteria of the genus Lactobacillus and Lactococcus.

In accordance with a preferred variant, the reaction is carried out in the presence of intact cells of microorganisms of the genus Lactobacillus, or intact cells of a recombinant microorganism which express an alpha-hydroxycarboxylic acid racemase activity according to the invention.

Preferred microorganisms are selected from among L. paracasei, L. delbrueckii, L. sakel and L. oris, in particular among the strains L. paracasei DSM 20207 and DSM 2649, L. delbrueckii DSM20074, L. sakei DSM 20017 and L. oris DSM 4864.

In a further preferred process variant, the enzyme is a lactate racemase (E.C.5.1.2.1) with a widened substrate spectrum, i.e. an enzyme which, in addition to (R)- or (S)-lactate racemizes at least one further (R)- or (S)-alpha-hydroxycarboxylic acid of the above formula I.

An enzyme activity which is useful in accordance with the invention encompasses, for example, the racemization of at least one selected from among the (R) and/or (S) form of phenyl lactate, 4-fluorophenyl lactate, 2-hydroxy-4-phenylbutyric acid, 2-hydroxy-4-methylpentanecarboxylic acid and 2-hydroxy-3-methylbutyric acid.

In a preferred embodiment of the above process, the desired stereoisomer is essentially removed, for example by chromatography, chemical or enzymatic stereoselective subsequent reaction and, if appropriate, further separation of the downstream product, from the isomer mixture formed, preferably after isolation of the mixture from the reaction medium, for example by chromatography, and the residue which essentially contains the undesired stereoisomer, is again isomerized. This can be repeated any number of times until a complete conversion into the desired stereoisomer, or the desired downstream product thereof, is obtained.

In a further preferred variant of the above process, the isomer mixture formed is subjected to a chemical or enzymatic stereoselective subsequent reaction, preferably after the mixture has been isolated from the reaction medium, for example by chromatography, and the reaction mixture obtained, which also contains the unreacted isomer of the hydroxycarboxylic acid, is subjected to another isomerization according to the invention. This can be repeated any number of times until a complete conversion into the desired stereoisomer, or the desired downstream product thereof, is obtained.

In a further preferred variant of the above process, the isomerization reaction is coupled with a chemical or enzymatic, enantioselective subsequent reaction, preferably in what is referred as a "one-pot reaction", where the resulting desired stereoisomer of the alpha-hydroxycarboxylic acid is removed stepwise or continuously from the reaction equilibrium.

Preferred chemical or enzymatic, enantioselective subsequent reactions after the isomerization step according to the invention are selected from among the esterification and the amidation of a stereoisomeric form of the alpha-hydroxycarboxylic acid. The subsequent enantioselective reaction can be performed, in particular, on a carboxyl or hydroxyl group.

A further aspect of the invention relates to a screening method for microorganisms which express an enzyme with alpha-hydroxycarboxylic acid racemase activity, in which a microorganism in which the racemase activity is suspected is cultured in the presence of a substrate comprising essentially a stereoisomeric form of an alpha-hydroxycarboxylic acid of the above formula I and the reaction medium is examined for racemization (for example diminishing quantity of one stereoisomeric form and/or increasing quantity of the other stereoisomeric form) of the substrate.

The screening method according to the invention is not limited to specific microorganisms. In principle, it can be carried out with all known eukaryotic and prokaryotic microorganisms, animal cells or plant cells. However, those microorganisms which form or metabolize lactate such as, for example, lactic acid bacteria or propionic acid bacteria, are preferred. Particularly suitable sources are bacteria of the genus *Lactobacillus*.

Microorganisms which are preferably screened are those which racemize the essentially stereoisomeric substrate to 1 to 100%, preferably to 20 to 100%, in particular 50 to 100% or 80 to 100% (racemization (%)=2R/(R+S)×100; R=concentration of the R form; S=concentration of the S form). Suitable conversion rates are in the range of from 1 to 50%, preferably 5 to 50%, in particular 15 to 50% or 30 to 50% (conversion rate (%)=R/(R+S)×100.

A further aspect of the invention relates to alpha-hydroxycarboxylic acid racemases which are capable of racemizing/isomerizing at least one compound of the above formula I and which are obtainable by culturing a microorganism which has tested positively for racemase activity in a screening method as defined above and isolating the alpha-hydroxycarboxylic acid racemate from the culture.

Especially preferred alpha-hydroxycarboxylic acid racemases are those which racemize at least one alpha-hydroxycarboxylic acid of the above formula I to 1 to 100%, preferably 20 to 100%, in particular 50 to 100%.

A further aspect of the invention relates to nucleic acid sequences encoding at least one alpha-hydroxycarboxylic acid racemase as defined above.

The invention furthermore relates to expression vectors comprising at least one coding nucleic acid sequence for an alpha-hydroxycarboxylic acid racemase in operable linkage with at least one regulatory nucleic acid sequence.

Aspect of the invention are also recombinant prokaryotic or eukaryotic microorganisms comprising at least one nucleic acid sequence as defined above or at least one expression vector as defined above.

A further aspect of the invention relates to a method for producing a protein with alpha-hydroxycarboxylic acid racemase activity, in which a recombinant microorganism as defined above, which expresses an enzyme with the desired racemase activity, is cultured and the protein is isolated from the culture.

Finally, the invention relates to a method for isolating a protein with alpha-hydroxycarboxylic acid racemase activity, in which a nonrecombinant microorganism as defined above, in particular of the genus *Lactobacillus*, which has tested positively for racemase activity is disrupted, cell wall debris is separated off and the protein with the desired enzyme activity is isolated.

DETAILED DESCRIPTION OF THE INVENTION

A. General Terms and Definitions

Unless specified otherwise, the following general conditions apply:

"Racemates" represent equimolar mixtures of the two enantiomers of an optically active compound.

In accordance with the invention, "racemization" or "isomerization" takes place at the alpha-carbon atom of the hydroxycarboxylic acid.

"Halogen" is fluorine, chlorine, bromine or iodine, in particular fluorine or chlorine.

"Lower alkyl" is preferably straight-chain or branched alkyl radicals having 2 to 8, in particular 2 to 6, carbon atoms such as ethyl, i- or n-propyl, n-, i-, sec- or tert-butyl, n-pentyl or 2-methylbutyl, n-hexyl, 2-methylpentyl, 3-methylpentyl, 2-ethylbutyl.

"Lower alkenyl" is the mono- or polyunsaturated, preferably monounsaturated, analog of the abovementioned alkyl radicals having 2 to 8, in particular 2 to 6, carbon atoms, it being possible for the double bond to be in any position of the carbon chain.

"Aryl" is a mono- or polynuclear, preferably mono- or binuclear, unsubstituted or substituted aromatic radical, in particular phenyl or else naphthyl which is bonded via any ring position, such as 1- or 2-naphthyl. If appropriate, these aryl radicals can have attached to them 1 or 2 identical or different substituents selected from among halogen, lower alkyl, lower alkoxy as defined above or trifluoromethyl.

B. Alpha-Hydroxycarboxylic Acids Capable of Undergoing Racemization alpha-Hydroxycarboxylic acids which, in accordance with the invention, can be converted by racemization are those alpha-hydroxycarboxylic acids of the above formula (I) where R is straight-chain or branched lower alkyl or lower alkenyl or —$(CH_2)_n$-Cyc where n is an integer of 0 to 4 and Cyc is an unsubstituted or mono- or polysubstituted, mono- or binuclear carbo- or heterocyclic ring. These compounds can be racemized in accordance with the invention in an enantiomerically pure form, i.e. as the R or S enantiomer, or as nonracemic mixture of the two enantiomers.

The alpha-hydroxycarboxylic acids of the formula I which are used for the enzymatic synthesis are compounds which are known per se and which can be obtained using generally known methods of organic synthesis.

Examples of carbo- and heterocyclic groups Cyc which must be mentioned are, in particular, mono- or binuclear, preferably mononuclear, groups having up to 4, such as, for example, 0, 1 or 2, identical or different ring heteroatoms selected among O, N and S.

These carbo- or heterocyclic rings encompass in particular 3 to 12, preferably 4, 5 or 6, ring carbon atoms. Examples which may be mentioned are cyclopropyl, cyclobutyl, cyclopentyl, cyclohexyl, cycloheptyl, their mono- or polyunsaturated analogs such as cyclobutenyl, cyclopentenyl, cyclopentadienyl, cyclohexenyl, cycloheptenyl, cyclohexadienyl, cycloheptadienyl, and phenyl; and 5- to 7-membered saturated or mono- or polyunsaturated heterocyclic radicals having 1 to 4 heteroatoms which are selected from among O, N and S. Heterocyclic radicals derived from pyrrolidine, tetrahydrofuran, piperidine, morpholine, pyrrole, furan, thiophene, pyrazole, imidazole, oxazole, thiazole, pyridine, pyran, pyrimidine, pyridazine and pyrazine must be mentioned in particular.

Others to be mentioned are binuclear radicals in which one of the abovementioned carbocycles or heterocycles is fused to a further heterocycle or carbocycle, such as, for example, radicals which are derived from cumarone, indole, quinoline and naphthalene.

In this context, the radicals Cyc can be bonded via any ring position, preferably via a ring carbon atom.

Examples of suitable Cyc radicals are phenyl, naphthyl, 2-thienyl, 3-thienyl; 2-furanyl, 3-furanyl; 2-pyridyl, 3-pyridyl or 4-pyridyl; 2-thiazolyl, 4-thiazolyl or 5-thiazolyl; 4-methyl-2-thienyl, 3-ethyl-2-thienyl, 2-methyl-3-thienyl, 4-propyl-3-thienyl, 5-n-butyl-2-thienyl, 4-methyl-3-thienyl, 3-methyl-2-thienyl; 3-chloro-2-thienyl, 4-bromo-3-thienyl, 2-iodo-3-thienyl, 5-iodo-3-thienyl, 4-fluoro-2-thienyl, 2-bromo-3-thienyl, and 4-chloro-2-thienyl.

The radicals Cyc can furthermore be monosubstituted or polysubstituted, such as, for example, monosubstituted or disubstituted. Preferably, the substituents are attached to a ring carbon atom. Examples of suitable substituents are halogen, lower alkyl, lower alkenyl, lower alkoxy, —OH, —SH, —$NO_2$ or $NR^2R^3$, where $R^2$ and $R^3$ independently of one another are H, methyl or ethyl. Preferred substituents are halogen radicals.

A further preferred group of Cyc radicals are aryl radicals as defined above.

C. Enzymes with Alpha-Hydroxycarboxylic Acid Racemase Activity

The enzymes with alpha-hydroxycarboxylic acid racemase activity in accordance with the invention can be obtained in particular from microorganisms of the genus *Lactobacillus*.

Preferred enzymes can be isolated from the *Lactobacillus* strains *L. paracasei* DSM 20207 (DSM 15755) and DSM 2649 (DSM 15751), *L. delbrueckii* DSM 20074 (DSM 15754), *L. sakei* DSM 20017 (DSM 15753) and *L. oris* DSM 4864 (DSM 15752). These strains are available from the DSMZ (Deutsche Sammlung von Mikroorganismen and Zellkulturen GmbH; German Collection of Microorganisms and Cell Cultures, Inhoffenstraβe 7 B, 38124 Braunschweig, Germany).

The enzymes can be isolated from cell cultures using customary preparative biochemical methods. Then, first amino acid sequence information can be deduced from the isolated enzymes in the customary manner, for example by peptide fragmentation and N-terminal sequencing.

Also encompassed by the invention are "functional equivalents" of the natural enzymes with alpha-hydroxycarboxylic acid racemase activity which can be isolated from the above organisms.

"Functional equivalents" or analogs of the natural racemases are, for the purposes of the present invention, polypeptides which differ from them but retain the desired biological activity such as, for example, substrate specificity. Thus, for example, "functional equivalents" are understood as meaning enzymes which racemize at least one compound selected from among phenyl lactate, 4-fluorophenyl lactate, 2-hydroxy-4-phenylbutyric acid, 2-hydroxy-4-methylpentanecarboxylic acid and 2-hydroxy-3-methylbutyric acid and which have at least 20%, preferably at least 50%, especially preferably at least 75%, very especially preferably at least 90% of the activity of a natural racemase enzyme from one of the abovementioned Lactobacillus strains or a higher activity than the latter. Moreover, functional equivalents are preferably stable from about pH 4 to 10 and advantageously have a pH optimum between pH 5 and 8 and a temperature optimum in the range of from 20° C. to 80° C.

"Functional equivalents" are, in accordance with the invention, in particular also understood as meaning mutants which have an amino acid which is not the natural amino acid in at least one sequence position of the natural amino acid sequences while retaining one of the abovementioned biological activities. Thus, "functional equivalents" encompass the mutants obtainable by one or more amino acid additions, substitutions, deletions and/or inversions, it being possible for the abovementioned modifications to occur in any sequence position as long as they lead to a mutant with the property profile according to the invention. In particular, functional equivalents also exist when the reactivity pattern between mutant and unmodified polypeptide agree in terms of quality, i.e. for example when identical substrates are converted at different rates.

"Functional equivalents" in the above sense are also "precursors" of the polypeptides described, and "functional derivatives" and "salts" of the polypeptides.

In this context, "precursors" are natural or synthetic precursors of the polypeptides with or without the desired biological activity.

The term "salts" is understood as meaning not only salts of carboxylic acid groups, but also addition salts of amino groups of the protein molecules according to the invention. Salts of carboxyl groups can be prepared in a manner known per se and encompass inorganic salts such as, for example, salts of sodium, calcium, ammonium, iron and zinc, and salts with organic bases such as, for example, amines, such as triethanolamine, arginine, lysine, piperidine and the like. Acid addition salts such as, for example, salts with mineral acids such as hydrochloric acid or sulfuric acid, and salts with organic acids such as acetic acid and oxalic acid, are likewise subject matter of the invention.

"Functional derivatives" of enzymes according to the invention can likewise be prepared on functional amino acid side groups or their N- or C-terminal end with the aid of known techniques. Such derivatives encompass, for example, aliphatic esters of carboxyl groups, amides of carboxyl groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

Naturally, "functional equivalents" also encompass polypeptides which can be obtained from other organisms, and naturally occurring variants. For example, regions of homologous sequences can be determined by sequence alignment, and equivalent enzymes can be established on the basis of the specific requirements of the invention.

"Functional equivalents" are additionally fusion proteins which have one of the natural racemase sequences or functional equivalents derived therefrom and at least one other heterologous sequence which is functionally different therefrom in functional N- or C-terminal linkage (i.e. without substantial mutual impairment of the function of the fusion protein moieties). Nonlimiting examples of such heterologous sequences are, for example, signal peptides or enzymes.

"Functional equivalents" also encompassed by the invention are homologs of the natural proteins. These have at least 60%, preferably at least 75%, in particular at least 85%, such as, for example, 90%, 95% or 99%, homology to one of the natural amino acid sequences, calculated by the algorithm of Pearson and Lipman, Proc. Natl. Acad. Sci. (USA) 85(8), 1988, 2444-2448. A percentage homology of a homologous polypeptide according to the invention means, in particular, percentage identity of the amino acid residues based on the total length of one of the amino acid sequences of an enzyme according to the invention or an enzyme subunit.

In the event of protein glycosylation, "functional equivalents" according to the invention encompass proteins of the above-specified type in deglycosylated or glycosylated form, and modified forms obtainable by changing the glycosylation pattern.

Homologs of the proteins or polypeptides according to the invention can be generated by mutagenesis, for example by point mutation or truncation of the protein.

Homologs of the racemases according to the invention can be identified by screening combinatorial libraries of mutants such as, for example, truncation mutants. For example, it is possible to generate a variegated library of protein variants by combinatorial mutagenesis at the nucleic acid level, such as, for example, by enzymatic ligation of a mixture of synthetic oligonucleotides. There is a large number of methods which can be used to generate libraries of potential homologs for a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide, in one mixture, all sequences which encode the desired set of potential protein sequences. Methods for synthesizing degenerate oligonucleotides are known to the skilled worker (for example Narang, S. A. (1983) Tetrahedron 39:3; Itakura et al. (1984) Annu. Rev. Biochem. 53:323; Itakura et al., (1984) Science 198: 1056; Ike et al. (1983) Nucleic Acids Res. 11:477).

The prior art knows a variety of techniques for screening gene products of combinatorial libraries which have been generated by point mutation or truncation, and for screening cDNA libraries for gene products with a selected characteristic. These techniques can be adapted to the rapid screening of the gene libraries which have been generated by combinatorial mutagenesis of homologs according to the invention. The most frequently used techniques for screening large gene libraries undergoing high-throughput analysis comprise the cloning of the gene library into replicable expression vectors, transforming suitable cells with the resulting vector library and expressing the combinatorial genes under conditions under which the detection of the required activity facilitates isolation of the vector which encodes the gene whose product has been detected, Recursive ensemble mutagenesis (REM), a technique which increases the frequency of functional mutants in the libraries, can be used in combination with the screening tests in order to identify homologs (Arkin and Yourvan (1992) PNAS 89:7811-7815; Delgrave et al. (1993) Protein Engineering 6(3):327-331).

D. Coding Nucleic Acid Sequences

The invention also relates to nucleic acid sequences which encode an enzyme with alpha-hydroxycarboxylic acid racemase activity. Preferred nucleic acid sequences are those which comprise the nucleic acid sequences derived from the natural amino acid sequences of the racemases which can be isolated from the above microorganisms.

All of the nucleic acid sequences according to the invention (single- and double-stranded DNA and RNA sequences such as, for example, cDNA and mRNA) can be generated from the nucleotide units in a manner known per se by chemical synthesis, such as, for example, by fragment condensation of individual overlapping complementary nucleic acid units of the double helix. The chemical synthesis of oligonucleotides can be carried out for example in the known manner using the phosphoamidite method (Voet, Voet, $2^{nd}$ Edition, Wiley Press New York, pages 896-897). Annealing synthetic oligonucleotides and filling in gaps with the aid of the DNA polymerase Klenow fragment, and ligation reactions, as well as general cloning methods, are described in Sambrook et al. (1989), Molecular Cloning: A laboratory manual, Cold Spring Harbor Laboratory Press.

In particular, the invention relates to nucleic acid sequences (single- and double-stranded DNA and RNA sequences such as, for example, cDNA and mRNA) encoding one of the enzymes according to the invention and their functional equivalents which are obtainable, for example, by using artificial nucleotide analogs.

The invention relates to both isolated nucleic acid molecules which encode polypeptides or proteins according to the invention or biologically active segments thereof, and to nucleic acid fragments which can be used, for example, for use as hybridization probes or primers for identifying or amplifying coding nucleic acids according to the invention.

The nucleic acid molecules according to the invention may additionally comprise untranslated sequences from the 3' and/or 5' end of the coding region of the gene.

The invention furthermore encompasses the nucleic acid molecules which are complementary to the nucleotide sequences described individually, or a segment of such a nucleic acid molecule.

The nucleic acid sequences according to the invention make possible the generation of probes and primers which can be used for identifying and/or cloning homologous sequences in other cell types and organisms. Such probes and primers usually comprise a nucleotide sequence region which hybridizes under stringent conditions (see hereinbelow) with at least approximately 12, preferably at least approximately 25, such as, for example, approximately 40, 50 or 75, consecutive nucleotides of a sense strand of a nucleic acid sequence according to the invention or of a corresponding antisense strand.

An "isolated" nucleic acid molecule is separated from other nucleic acid molecules which are present in the natural source of the nucleic acid and may, moreover, be essentially free of other cellular material or culture medium if produced by recombinant techniques, or free of chemical precursors or other chemicals if chemically synthesized.

A nucleic acid molecule according to the invention can be isolated by using standard techniques of molecular biology and the sequence information provided in accordance with the invention. For example, cDNA can be isolated from a suitable cDNA library by using one of the specifically disclosed complete sequences or a segment thereof as hybridization probe and standard hybridization techniques (such as, for example, described in Sambrook, J., Fritsch, E. F. and Maniatis, T. Molecular Cloning: A Laboratory Manual. $2^{nd}$ Ed., Cold Spring Harbor Laboratory, Cold Spring Harbor Laboratory Press, Cold Spring Harbor, N.Y., 1989). Moreover, it is possible for a nucleic acid molecule comprising one of the disclosed sequences, or a segment of such a molecule, to be isolated by polymerase chain reaction using the oligonucleotide primers which have been generated on the basis of this sequence. The nucleic acid amplified in this way can be cloned into a suitable vector and characterized by DNA sequence analysis. The oligonucleotides according to the invention can furthermore be generated by standard synthetic method, for example using an automatic DNA synthesizer.

In principle, the nucleic acid sequences according to the invention can be identified and isolated from all organisms. The nucleic acid sequences according to the invention can advantageously be isolated from bacteria of the abovementioned type.

Nucleic acid sequences according to the invention or derivatives thereof, homologs or parts of these sequences can be isolated from other microorganisms for example using customary hybridization methods or PCR technology, for example via genomic libraries or cDNA libraries. These DNA sequences hybridize with the sequences according to the invention under standard conditions. It is advantageous to use short oligonucleotides of the conserved regions, for example the active center, which can be identified via comparisons with alpha-hydroxycarboxylic acid racemase in the manner known to the skilled worker, for the hybridization. Alternatively, longer fragments of the nucleic acids according to the invention, or the complete sequences, may be used for the hybridization. Depending on the nucleic acid used (oligonucleotide, longer fragment or complete sequence), or depending on the type of nucleic acid (DNA or RNA) being used for the hybridization, these standard conditions vary. Thus, for example, the melting points for DNA:DNA hybrids are approximately 10° C. lower than those of DNA:RNA hybrids of the same length.

For example, standard conditions are understood as meaning, depending on the nucleic acid, temperatures between 42 and 58° C. in an aqueous buffer solution at a concentration of from 0.1 to 5×SSC (1×SSC=0.15 M NaCl, 15 mM sodium citrate, pH 7.2) or additionally in the presence of 50% formamide, such as, for example, 42° C. in 5×SSC, 50% formamide. For DNA:DNA hybrids, the hybridization conditions are advantageously 0.1×SSC and temperatures of from approximately 20° C. to 45° C., preferably from approximately 30° C. to 45° C. For DNA:RNA hybrids, the hybridization conditions are advantageously 0.1×SSC and temperatures from approximately 30° C. to 55° C., preferably from approximately 45° C. to 55° C. These temperatures which have been stated for the hybridization are melting points which have been calculated by way of example for a nucleic acid with a length of approximately 100 nucleotides and a G+C content of 50% in the absence of formamide. The experimental conditions for DNA hybridization are described in relevant textbooks of genetics, such as, for example, Sambrook et al., "Molecular Cloning", Cold Spring Harbor Laboratory, 1989, and can be calculated using formulae known to the skilled worker, for example as a function of the length of the nucleic acids, the type of hybrid or the G+C content. Further information on hybridization can be found by the skilled worker in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The invention also relates to derivatives of the specifically disclosed or derivable nucleic acid sequences.

Thus, further nucleic acid sequences according to the invention can be derived from the natural sequences and differ therefrom through addition, substitution, insertion or deletion of one or more nucleotides, while still encoding polypeptides with the desired profile of characteristics.

Also encompassed in accordance with the invention are those nucleic acid sequences which comprise what are known as silent mutations or which are modified, in comparison with a specifically mentioned sequence, in accordance with the codon usage of a specific source of origin or host organism, as are naturally occurring variants such as, for example, splice variants or allelic variants, thereof.

Sequences which can be obtained by conservative nucleotide substitutions (i.e. the amino acid in question is replaced by an amino acid with the same charge, size, polarity and/or solubility) are also subject matter.

The invention also relates to the molecules derived from the specifically disclosed nucleic acids by sequence polymorphisms. These genetic polymorphisms may exist within individuals within a population owing to the natural variation. These natural variations usually bring about a variance of 1 to 5% in the nucleotide sequence of a gene.

Derivatives of the nucleic acids according to the invention are understood as meaning, for example, allelic variants with at least 40% homology at the deduced amino acid level, preferably 60% homology, very especially preferably at least 80% homology, over the entire sequence region (with regard to homology at the amino acid level, reference may be made to the above explanation regarding polypeptides). Advantageously, the homology levels can be higher over part-regions of the sequences.

Derivatives are also understood as meaning homologs of the nucleic acid sequences according to the invention, for example fungal or bacterial homologs, truncated sequences, single-strand DNA or RNA of the coding and noncoding sequence. Thus, for example, homologs to SEQ ID NO: 1 have at least 40% homology at the DNA level, preferably at least 60%, especially preferably at least 70%, very especially preferably at least 80% over the entire DNA region stated in SEQ ID NO: 1.

Derivatives are, moreover, understood as meaning for example fusions with promoters. The promoters which precede the abovementioned nucleotide sequences can have been modified through one or more nucleotide substitutions, insertions, inversions and/or deletions without, however, adversely affecting the functionality or efficacy of the promoters. Moreover, the efficacy of the promoters can be increased by modifying their sequence, or the promoters can be substituted completely by more efficient promoters, including those from heterologous organisms.

Derivatives are also understood as meaning variants whose nucleotide sequence in the region of from −1 to −1000 bases upstream of the start codon, or 0 to 1000 bases downstream of the stop codon, have been modified in such a way that gene expression and/or protein expression is modified, preferably increased.

The invention furthermore relates to nucleic acid sequences which hybridize with the abovementioned coding sequences under "stringent conditions". These polynucleotides can be identified when screening genomic libraries or cDNA libraries and, if appropriate, amplified by means of PCR using suitable primers and subsequently isolated, for example with suitable probes. Moreover, polynucleotides according to the invention may also be synthesized chemically. This characteristic is understood as meaning the ability of a poly- or oligonucleotide to bind under stringent conditions to an almost complementary sequence, while there are no nonspecific bindings between noncomplementary partners under these conditions. For this purpose, the sequences should have 70-100%, preferably 90-100%, complementarity. The characteristic of complementary sequences being able to bind specifically to one another is exploited, for example, in Northern or Southern blot technique or in PCR or RT-PCR in the case of primer binding. Usually, oligonucleotides with a length of 30 base pairs or more are employed for this purpose. Stringent conditions are understood as meaning, for example in the Northern blot technique, the use of a washing solution at a temperature of 50-70° C., preferably 60-65° C., for example 0.1×SSC buffer with 0.1% SDS (20× SSC:3M NaCl, 0.3M Na citrate, pH 7.0) for eluting nonspecifically hybridized cDNA probes or oligonucleotides. In this case, as mentioned above, only nucleic acids with a high degree of complementarity remain bound to one another. The setting up of stringent conditions is known to the skilled worker and described, for example, in Ausubel et al., Current Protocols in Molecular Biology, John Wiley & Sons, N.Y. (1989), 6.3.1-6.3.6.

E. Constructs According to the Invention

The invention furthermore relates to expression constructs comprising, under the genetic control of regulatory nucleic acid sequences, a nucleic acid sequence encoding an enzyme of the invention; and to vectors comprising at least one of these expression constructs.

Such constructs according to the invention preferably encompass a promoter 5'-upstream from the particular coding sequence and a terminator sequence 3'-downstream, and, where appropriate, further customary regulatory elements, in each case linked operably to the coding sequence.

"Operable linkage" is understood as meaning the sequential arrangement of promoter, coding sequence, terminator and, where appropriate, other regulatory elements in such a way that each of the regulatory elements is able to comply with the intended function in the expression of the coding sequence. Examples of sequences capable of operable linkage are targeting sequences, and also enhancers, polyadenylation signals and the like. Other regulatory elements comprise selectable markers, amplification signals, origins of replication and the like. Suitable regulatory sequences are described, for example, in Goeddel, Gene Expression Technology: Methods in Enzymology 185, Academic Press, San Diego, Calif. (1990).

A nucleic acid construct according to the invention is understood as meaning in particular the natural alpha-hydroxycarboxylic acid racemase genes and the derivatives and homologs thereof, which have been linked operably or functionally with one or more regulatory signals, advantageously for controlling, for example increasing, gene expression.

In addition to these regulatory sequences, the natural regulation of these sequences may still be present before the actual structural genes and, if appropriate, may have been genetically modified so that the natural regulation has been switched off and expression of the genes increased. However, the nucleic acid construct may also be simpler in construction, that is to say that no additional regulatory signals have been inserted before the coding sequence and the natural promoter together with its regulation has not been removed. Instead, the natural regulatory sequence is mutated in such a way that regulation no longer takes place and gene expression is increased.

A preferred nucleic acid construct advantageously also comprises one or more of the abovementioned enhancer sequences in operable linkage with the promoter, which make possible enhanced expression of the nucleic acid sequence. At the 3' end of the DNA sequences, too, additional advantageous sequences, such as further regulatory elements or terminators, may be inserted. One or more copies of the nucleic acids according to the invention may be present in the construct. Further markers, such as resistances to antibiotics, or auxotrophism-complementing genes, may additionally be present, if appropriate, for selection for the construct.

Advantageous regulatory sequences for the method according to the invention are present for example in promoters such as cos, tac, trp, tet, trp-tet, lpp, lac, lpp-lac, lacI$^{q-}$,T7, T5, T3, gal, trc, ara, rhaP (rhaP$_{BAD}$)SPO6, lambda-P$_R$ or lambda-P$_L$ promoter, which are preferably employed in Gram-negative bacteria. Other advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for the regulation.

For expression in a host organism, the nucleic acid construct is advantageously inserted into a vector, such as for example a plasmid or a phage, which makes possible optimal expression of the genes in the host. Vectors are understood as meaning, in addition to plasmids and phages, all other vectors known to the skilled worker, that is to say, for example, viruses such as SV40, CMV, baculovirus and adenovirus, transposons, IS elements, phasmids, cosmids, and linear or circular DNA. These vectors are capable of undergoing autonomous replication in the host organism or chromosomal replication. These vectors constitute a further embodiment of the invention. Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeast 2alphaM, pAG-1, YEp6, YEp13 or pEMBLYe23 or in plants pLGV23, pGHlac$^+$, pBIN19, pAK2004 or pDH51. The abovementioned plasmids are a small selection of plasmids which are possible. Other plasmids are well known to the skilled worker and can be found, for example, in the book Cloning Vectors (Eds. Pouwels P. H. et al. Elsevier, Amsterdam-New York-Oxford, 1985, ISBN 0 444 904018).

For the expression of the further genes which are present, the nucleic acid construct advantageously additionally comprises 3'- and/or 5'-terminal regulatory sequences for enhancing expression, and such sequences are selected for optimal expression as a function of the chosen host organism and the gene, or genes.

These regulatory sequences are intended to make possible the specific expression of the genes and protein expression. Depending on the host organism, this may mean, for example, that the gene is expressed, or overexpressed, only after induction, or that it is immediately expressed and/or overexpressed.

The regulatory sequences or factors may preferably have a positive effect on, and thus enhance, the gene expression of the gene introduced. Thus, enhancement of the regulatory elements can take place advantageously at the transcriptional level by using strong transcription signals such as promoters and/or enhancers. However, it is also possible to enhance translation, for example by improving the stability of the mRNA.

In a further embodiment of the vector, the vector comprising the nucleic acid construct according to the invention or the nucleic acid according to the invention may advantageously also be introduced into the microorganisms in the form of a linear DNA and integrated into the genome of the host organism via heterologous or homologous recombination. This linear DNA may consist of a linearized vector, such as a plasmid, or only of the nucleic acid construct or the nucleic acid according to the invention.

For the optimal expression of heterologous genes in organisms, it is advantageous to modify the nucleic acid sequences in accordance with the specific codon usage used in the organism. Codon usage can be determined readily with the aid of computer evaluations of other, known genes of the organism in question.

An expression cassette according to the invention is prepared by fusing a suitable promoter to a suitable codon nucleotide sequence and a terminator signal or polyadenylation signal. Conventional recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al:, Current Protocols in Molecular Biology, Greene Publishing Assoc. and Wiley Interscience (1987) are used for this purpose.

For expression in a suitable host organism, the recombinant nucleic acid construct or gene construct is advantageously inserted into a host-specific vector which makes possible the optimal expression of the genes in the host. Vectors are well known to the skilled worker and can be found in, for example, "Cloning Vectors" (Pouwels P. H. et al., Ed., Elsevier, Amsterdam-New York-Oxford, 1985).

F. Hosts which are Useful in Accordance with the Invention

The vectors according to the invention allow the generation of recombinant microorganisms which are transformed for example with at least one vector according to the invention and which can be employed in the production of the enzymes according to the invention. The above-described recombinant constructs according to the invention are advantageously introduced into a suitable host system, where they are expressed. In this context, cloning and transfection methods with which the skilled worker is familiar, such as coprecipitation, protoplast fusion, electroporation, retroviral transfection and the like, are used in order to express the abovementioned nucleic acids in the expression system in question. Suitable systems are described, for example, in Current Protocols in Molecular Biology, F. Ausubel et al., Ed., Wiley Interscience, New York 1997, or Sambrook et al. Molecular Cloning: A Laboratory Manual. 2. ed., Cold Spring Harbor Laboratory, Cold Spring Harbor Laboratory Press, Cold Spring Harbor, N.Y., 1989.

Microorganisms which have undergone homologous recombination can also be prepared in accordance with the invention. To this end, a vector is prepared which contains at least one segment of a gene according to the invention or of a coding sequence, into which, if appropriate, at least one amino acid deletion, addition or substitution has been introduced in order to modify, for example functionally to disrupt, the sequence according to the invention ("knockout" vector). The sequence introduced may, for example, also be a homolog from a related microorganism or else derived from a mammalian, yeast or insect source. However, the vector used for homologous recombination may also be designed in such a way that the endogenous gene is mutated or otherwise modified upon homologous recombination, while still encoding the functional protein (for example, the upstream regulatory region can be modified in such a way that the expression of the endogenous protein is thus modified). The modified segment of the gene according to the invention is present in the homologous recombination vector. The construction of suitable vectors for homologous recombination is described, for example, in Thomas, K. R. and Capecchi, M. R. (1987) Cell 51:503.

Suitable recombinant host organisms for the nucleic acid according to the invention or the nucleic acid construct are, in principle, all prokaryotic or eukaryotic organisms. Microorganisms such as bacteria, fungi or yeasts are advantageously used as host organisms. Gram-positive or Gram-negative bacteria are advantageously used. The genus and species *Escherichia coli* is very especially preferred.

The host organism, or host organisms, according to the invention preferably comprise at least one of the nucleic acid sequences, nucleic acid constructs or vectors which are described in the present invention and which encode an enzyme with alpha-hydroxycarboxylic acid racemase activity.

Depending on the host organism, the organisms used in the method according to the invention are cultured or grown in the manner with which the skilled worker is familiar. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese, magnesium, and, if appropriate, vitamins, at temperatures of from 0° C. to 100° C., preferably from 10° C. to 60° C., while passing in oxygen. The pH of the liquid nutrient medium can be kept constant, i.e. regulated during the culture period, or not. The microorganisms can be cultured batchwise, semibatchwise or continuously. Nutrients can be provided at the beginning of the fermentation or fed in semicontinuously or continuously. The ketone can be added directly during the culturing period or advantageously thereafter. The enzymes can be isolated from the organisms by the methods described in the examples or else used for the reaction in the form of a crude extract.

G. Recombinant Production of the Enzymes According to the Invention:

The invention furthermore relates to methods for the recombinant production of polypeptides according to the invention or of functional, biologically active fragments thereof, in which method a polypeptide-producing microorganism is cultured, expression of the polypeptides is induced, if appropriate, and the polypeptides are isolated from the culture. If desired, the polypeptides can also be produced on an industrial scale in this manner.

The recombinant microorganism can be cultured and fermented by known methods. Bacteria can be multiplied for example in TB or LB medium and at a temperature of from 20 to 40° C. and a pH value of 6 to 9. The individual cultivation conditions which are suitable are described, for example, in T. Maniatis, E. F. Fritsch and J. Sambrook, Molecular Cloning: A Laboratory Manual, Cold Spring Harbor Laboratory, Cold Spring Harbor, N.Y. (1989).

Unless the polypeptides are secreted into the culture medium, the cells are then disrupted and the product is obtained from the lysate by known protein isolation methods.

The cells can be disrupted either by high-frequency ultrasound, by high pressure, such as, for example, in a French pressure cell, by osmolysis, by allowing detergents, lytic enzymes or organic solvents to act on them, by homogenizers or by combining several of the abovementioned methods.

The polypeptides can be purified with known chromatographic methods, such as molecular sieve chromatography (gel filtration), such as Q-sepharose chromatography, ion exchange chromatography and hydrophobic chromatography, or else by other customary methods such as ultrafiltration, crystallization, salting out, dialysis and native gel electrophoresis. Suitable methods are described, for example, in Cooper, F. G., Biochemische Arbeitsmethoden [Methods in Biochemistry], Verlag Walter de Gruyter, Berlin, N.Y. or in Scopes, R., Protein Purification, Springer Verlag, New York, Heidelberg, Berlin.

To isolate the recombinant protein, it may be advantageous to employ vector systems or oligonucleotides which extend the cDNA by specific nucleotide sequences and thus encode modified polypeptides or fusion proteins which serve, for example, for simpler purification. Such suitable modifications are, for example, what are known as "Tags" which act as anchors, such as, for example, the modification known as hexa-histidine anchor, or epitopes which can be recognized by antibodies as antigens (described for example in Harlow, E. and Lane, D., 1988, Antibodies: A Laboratory Manual. Cold Spring Harbor (N.Y.) Press). These anchors can serve for attaching proteins to a solid support, such as, for example, a polymer matrix, which, for example, may be used for packing a chromatography column, or else to a microtiter plate or any other support.

These anchors can simultaneously also be used for identifying the proteins. Moreover, customary tags, such as fluorescent dyes, enzyme tags which, after reaction with a substrate, form a detectable reaction product, or radiolabels, alone or in combination with the anchors, may additionally be used for identifying the proteins in order to derivatize the proteins.

H. Nonrecombinant Isolation of the Enzymes According to the Invention

Enzymes according to the invention are expediently isolated from one of the above-described natural sources (*Lactobacillus* strains) or from another microorganism which expresses alpha-hydroxycarboxylic acid racemase activity and which has been identified with the aid of a screening method according to the invention.

The microorganism can be cultured and fermented by known methods. Unless the polypeptides are secreted into the culture medium, the cells are then disrupted and the product is obtained from the lysate by known protein isolation methods. The cells can be disrupted either by high-frequency ultrasound, by high pressure, such as, for example, in a French pressure cell, by osmolysis, by allowing detergents, lytic enzymes or organic solvents to act on them, by homogenizers or by combining several of the abovementioned methods.

The polypeptides can be purified with known chromatographic methods, such as molecular sieve chromatography (gel filtration), such as Q-sepharose chromatography, ion exchange chromatography and hydrophobic chromatography, or else by other customary methods such as ultrafiltration, crystallization, salting out, dialysis and native gel electrophoresis. Suitable methods are described, for example, in Cooper, F. G., Biochemische Arbeitsmethoden [Methods in Biochemistry], Verlag Walter de Gruyter, Berlin, N.Y. or in Scopes, R., Protein Purification, Springer Verlag, New York, Heidelberg, Berlin.

I. Carrying Out the Method According to the Invention for the Isomerization of Alpha-Hydroxycarboxylic Acids The enzymes with alpha-hydroxycarboxylic acid racemase activity can be used in the method according to the invention as the free enzyme or as an immobilized enzyme.

The method according to the invention is advantageously carried out at a temperature of from 0° C. to 95° C., preferably from 10° C. to 85° C., especially preferably from 15° C. to 75° C., in particular 25 to 40° C.

The pH value in the method according to the invention is advantageously maintained at from pH 4 to 12, preferably from pH 4.5 to 9, especially preferably from pH 5 to 8.

The method according to the invention may employ growing cells which comprise nucleic acids, nucleic acid constructs or vectors according to the invention. Alternatively, quiescent or disruptive cells may be used. Disruptive cells are understood as meaning, for example, cells which have been made permeable via treatment with, for example, solvents, or else cells which have been disrupted via enzyme treatment, via methanical treatment (for example French press or ultrasound) or via any other method. The crude extracts thus obtained are advantageously suitable for the method according to the invention. Fully or partially purified enzymes may also be used for the method. Immobilized microorganisms or enzymes are likewise suitable, and these can be employed advantageously reaction.

If free organisms or immobilized enzymes are used for the method according to the invention, they are expediently separated off before the extraction step, for example via filtration or centrifugation.

The product prepared in the method according to the invention can be recovered advantageously from the aqueous reaction solution by extraction or distillation. An extraction step can be repeated several times in order to increase yield. Examples of suitable extractants are customary solvents with which the skilled worker is familiar, such as toluene, methylene chloride, diisopropyl ether, benzene, MTBE or ethyl acetate, without imposing any limitation.

After concentration of the organic phase, the products can, as a rule, be recovered in good chemical purity, i.e. a chemical purity of more than 80%. However, the organic phase containing the product may, after extraction, also be only partially concentrated and the product can be crystallized out. To this end, the solution is advantageously cooled down to a temperature of from 0° C. to 10° C. However, crystallization can also be effected directly from the organic solution or from an aqueous solution. The product which has crystallized out can be taken up again in the same or a different solvent for recrystallization and be recrystallized.

The method according to the invention can be operated batchwise, semibatchwise or continuously.

The method can advantageously be carried out in bioreactors such as, for example, described in Biotechnology, Volume 3, $2^{nd}$ Edition, Rehm et al. (ed.), (1993), in particular chapter II.

K. Further Applications of the Invention

The present invention opens up a multiplicity of further possible applications of the isomerization reactions according to the invention. The following examples may be mentioned with imposing any limitation:

a) Racemization of alpha-hydroxycarboxylic acids for "recycling" the undesired stereoisomer in traditional racemate separations after removal of the desired product. The advantage is the neat enzymatic racemization reaction; in contrast, chemically catalyzed racemization reactions usually proceed under drastic reaction conditions which lead to decomposition, to the formation of secondary products and to side reactions (elimination and the like). (Compare also: Kontrollierte Racemisierung von organischen Verbindungen [Controlled racemization of organic compounds]: E. J. Ebbers, G. J. A. Ariaans, J. P. M. Houbiers, A. Bruggink, B. Zwanenburg, *Tetrahedron*, 1997, 53, 9417-9476)

b) Step deracemization of alpha-hydroxycarboxylic acids. If the racemase cannot be employed directly in a "one-pot process" in a (chemically or enzymatically catalyzed) enantioselective step (for example owing to the reaction conditions required), the enzymatic racemization is carried out after the enantioselective step without separating the enantiomeric product (cf. analogous example using mandelate racemase: U. T. Strauss, K. Faber, *Tetrahedron: Asymmetry*, 1999, 10, 4079-4081).

c) The ideal case of an application corresponds to a direct combination of the racemase with a chemo- or biocatalytic step in a "one-pot process", which is known as "dynamic racemate separation". Such methods are sophisticated and extremely effective.

The following may be mentioned as examples of an enantioselective step which can be combined with a racemization according to the invention:

(i) lipase-catalyzed esterification, for example acyl transfer reaction (U. T. Strauss, K. Faber, *Tetrahedron: Asymmetry*, 1999, 10, 4079-4081).

(ii) lipase- or protease-catalyzed amide formation (F. van Rantwijk, M. A. P. J. Hacking, R. A. Sheldon, *Monatsh. Chem./Chem. Monthly*, 2000, 131, 549-569.)

The above description and the examples which follow are merely intended to illustrate the invention. The large number of possible modifications which are obvious to the skilled worker also come within the scope of the invention.

Experimental Part

A. General Information

1. Equipment and Methods Used

Thin-Layer Chromatography

The reactions are monitored, and the purity of the products is examined, by thin-layer chromatography. Silica gel $60_{F254}$ on aluminum foil, from Merck, was used for this purpose. Detection was carried out both by UV light (254 mm) and by spraying with molybdate solution [$(NH_4)_6Mo_7O_{24} \times 4H_2O$ (100 g/l) and $Ce(SO_4)_2 \times 4H_2O$ (4 g/l) in $H_2SO_4$ (10%)], followed by heating.

Column Chromatography

The racemization products are purified by column chromatography. Silica gel with a particle size of 43-63 µm from Merck was used as stationary phase for this purpose. Mixtures of petroleum ether (PE) and ethyl acetate (EA) were employed as eluents, the composition being adapted to suit the separation problem in question. Separation was carried out under elevated pressure.

Gas Chromatography

The gas-chromatographic separation of the racemization products was carried out using a Varian gas chromotograph 3800-split/splitless injector (FID). The column used was a Chirasil-DEX, Chrompack, permethyl-β-cyclodextrin, chemically bound, 25 m×0.32 mm×0.25 µm, $H_2$. Examples of suitable separation conditions are shown in Table 1 which follows

TABLE 1

Separation of enantiomers using chiral GC

| Compound | Inlet pressure [psi] | Temperature program [° C.] | Retention time [min] |
| --- | --- | --- | --- |
| Lactate | 12 | 45° C. | 4.6 (R) |
|  |  |  | 6.0 (S) |
| Phenyl lactate | 12 | 125° C. | 7.5 (R) |
|  |  |  | 8.5 (S) |
| 4-Fluorophenyl lactate | 12 | 80° C./0-5° C./min | 12.0 (R) |
|  |  | 170° C. | 12.5 (S) |

NMR $^1$H— and $^{13}$C NMR spectra were recorded using a Bruker 360 or 500 MHz; the chemical shifts are shown in ppm (δ scale); tetramethylsilane (TMS) was used as the internal standard.

HPLC

The e.e. values were determined via a JASCO HPLC system type PU-980 pumps and an MD 910 UV detector. A DAICEL Chiralpack AD (0.46 cm×25 cm) column was used for the separation.

Melting Points

The melting points were determined using an MPD 350.BML.5 from GALLENKAMP.

2. Microbiological Methods and Materials 2.1 Growing the Cultures

Bacterial Strains

Table 2 contains a list of the strains studied, their culture conditions and their deposit numbers.

TABLE 2

Growth conditions of bacterial strains studied

| Strain | DSM number | Medium | Temperature |
| --- | --- | --- | --- |
| L. haloferax volcanii | 5176 | 372 | 37° C. |
| L. haloarcula vallismortis | 3756 | 372 | 37° C. |
| L. paracasei | 20008 | 11 | 30° C. |
| L. paracasei | 20207 | 11 | 30° C. |
| L. paracase | 2649 | 11 | 30° C. |
| L. acidophilus | 20079 | 11 | 30° C. |
| L. brevis | 20054 | 11 | 30° C. |
| L. piscicola | 20722 | 92 | 30° C. |
| L. halotolerans | 20190 | 11 | 30° C. |
| L. confusus | 20196 | 11 | 30° C. |
| L. acetotolerans | 20749 | 231 | 30° C. |
| L. delbrueckii ssp. delbrueckii | 20074 | 11 | 37° C. |
| L. kandleri | 20593 | 11 | 30° C. |
| L. fructosus | 20349 | 11 | 30° C. |
| L. farciminis | 20184 | 11 | 30° C. |
| L. gasseri | 20243 | 11 | 37° C. |
| L. alimentarius | 20249 | 11 | 30° C. |
| L. jensenii | 20557 | 11 | 37° C. |
| L. curvatus | 20010 | 11 | 30° C. |
| L. sakei ssp. sakei | 20017 | 11 | 30° C. |
| L. oris | 4864 | 11 | 37° C. |

Strain Maintenance

Strains were maintained by freezing the cells in specific cryosolutions. To this end, the culture was transferred into sterile centrifuge tubes and centrifuged for 30 minutes at 8000 rpm and 4° C., and the supernatant solution was decanted off. Thereafter, the cells were suspended in cryosolution, transferred into sterile vials and maintained at −70° C. The cryosolution used was either a solution of 20% by volume DMSO and 0.7% by weight of NaCl in $H_2O$ (Sölkner), or glycerol with 5% by volume of $H_2O$ (Weigers).

Growing the Strains

The cultures were grown in 1000 ml Erlenmeyer flasks in a drying oven at 30° C. or 37° C. (depending on the bacterial strain). For each bacterial strain, 1 liter of the sterile medium in question was first divided into four flasks and inoculated with in each case 500 µl of the cell solution which had previously been defrosted. All sterile steps of the procedure were carried out in a laminar-flow clean bench (Heraeus "Herasafe", type HS9).

Harvesting the Cells

After a growth phase of 3 to 15 days, depending on the bacterial strain, the cells were harvested. To this end, the culture was transferred into centrifuge tubes and centrifuged for 20 minutes at 8000 rpm and 4° C., and the supernatant was decanted off. To wash the cells, they were suspended in approximately 40 ml of buffer (50 mM Bis-Tris, 0.01 M $MgCl_2$, pH=6) and centrifuged for another 20 minutes. The washing procedure was performed twice. The cells were subsequently resuspended in a little buffer, transferred into a round-bottom flask and shock-frozen. This was done by swirling the flask in a Dewar vessel filled with liquid nitrogen. Freeze-drying was carried out in a lyophilizer from Braun ("Christ Alpha 1-4"). The lyophilized cells were transferred into glass flasks and stored in the fridge until used.

2.2 Nutrient Media and Sterilization

The nutrient media recommended for the bacterial strains in question were used for growing the microorganisms. The media were sterilized prior to inoculation by autoclaving (Varioklav steam sterilizer, H+P Labortechnik GmbH, Munich) at 121° C. and a superatmospheric pressure of 1 bar.

Medium 11

Medium 11 was used as nutrient medium for the following bacterial strains: *L. paracasei, L. acidophilus, L. brevis, L. halotolerans, L. confusus, L. farciminis, L. gasseri, L. alimentarius, L. jensenli, L. delbrueckii, L. curvatus, L. sakei* ssp. *sakei, L. kandeleri* and *L. fructosus*.

Table 3 shows the composition of the medium. To prevent a possible Maillard reaction and precipitation of the salts, the components of the media were sterilized separately and combined after sterilization only. A Maillard reaction occurs when compounds such as reducing sugars react with amino acids and proteins, and it causes a dark coloration of the medium.

TABLE 3

Composition of medium 11

| Substance | Concentration [g/l] |
|---|---|
| Casein peptone (Oxoid) | 10.00 |
| Peptone (Oxoid) | 10.00 |
| Yeast extract (Oxoid) | 5.00 |
| Glucose | 20.00 |
| $K_2HPO_4$ | 2.00 |
| Sodium acetate trihydrate | 8.00 |
| Ammonium citrate | 2.00 |
| $MgSO_4 \times 7H_2O$ | 0.20 |
| $MnSO_4 \times H_2O$ | 0.05 |
| Tween 80 | 1.00 |

Medium 231

Medium 231, which differs from medium 11 only in terms of the pH value, was used for *L. acetotolerans*. The components listed in Table 3 were combined and only then sterilized, and the pH was adjusted to 5.2.

Medium 92

Medium 92 was used for *L. piscicola*. Its composition is shown in Table 4.

TABLE 4

Composition of medium 92

| Substance | Concentration [g/l] |
|---|---|
| Soya extract, tryptic digest (Oxoid) | 30.00 |
| Yeast extract (Oxoid) | 3.00 |

Medium 372

Medium 372 was used for the strains *Haloferax volcanii* and *Haloarcula vallismortis*.

TABLE 5

Composition of medium 372

| Substance | Concentration [g/l] |
|---|---|
| Yeast extract (Oxoid) | 5.00 |
| Casamino acids (Oxoid) | 5.00 |
| Sodium glutamate (Oxoid) | 1.00 |
| KCl | 2.00 |
| Sodium citrate | 3.00 |
| $MgSO_4 \times 7H_2O$ | 20.00 |
| NaCl | 200.00 |
| $FeCl_2 \times 4H_2O$ | 0.036 |
| $MnCl_2 \times 4H_2O$ | 0.00036 |

B. Experiments Carried Out

EXAMPLE 1

Synthesis of Substrates and Reference Material a) Synthesis of Enantiomerically Pure 2-hydroxy-3-phenylpropionate Reaction mixture: 1 g of enantiomerically pure phenylalanine (6.05 mmol) is dissolved in 12 ml of $H_2SO_4$ (1M). 1.66 g (24 mmol) of $NaNO_2$ are added portionwise with ice-cooling. After the addition, the cooling system is removed and stirring of the reaction mixture is continued overnight at room temperature.

Work-up: The aqueous solution is extracted three times using 4 ml of ethyl ether in each case, the organic phase is washed with saturated sodium chloride solution, and the sodium chloride solution is reextracted once with ethyl ether. The combined organic phase is dried over $Na_2SO_4$ and the solvent is evaporated on a Rotavapor. The yellow oily residue is treated with 2 ml of hexane and crystallized by scraping with a glass rod. A precipitate of white crystals forms. The crystals are washed three times using approximately 2 ml of hexane, and the remainder of the solvent is evaporated on a rotary evaporator.

Optical rotation (literature): (S)-phenyl lactate: $[\alpha]_D^{25}$=−20.8 (c=2, H$_2$O)

(R)-phenyl lactate: $[\alpha]_D^{25}$=+20.9 (c=2.3 H$_2$O)

b) Synthesis of rac-4-fluorophenyl lactate rac-3

Reaction mixture: 400 mg (2.2 mmol) of rac-4-fluorophenylalanine, 670 mg (9.7 mmol) of NaNO$_2$ in 4.8 ml H$_2$SO (1M).

Yield: 197 mg (49.0%), white crystals $^1$H NMR: (360 MHz, CDCl$_3$) δ=2.97 (1H, dd, J$_1$=7.2 Hz, J$_2$=14.4 Hz, CH$_2$); 3.17 (1H, dd, J$_1$=3.6 Hz, J$_2$=14.4 Hz, CH$_2$); 4.49 (1H, dd, J$_1$=3.6 Hz, J$_2$=6.1 Hz, CH—OH); 6.98-7.02 (2H, m, Ar); 7.20-7.28 (2H, m, Ar).

$^{13}$C NMR: (90 MHz, CDCl$_3$) δ=39.2 (CH$_2$); 70.9 (CH—OH); 115.3 (d, J=21.6 Hz, Ar-m); 130.9 (d, J=21.6 Hz, Ar-o); 131.6 (d, J=3.6 Hz, Ar-i); 162.1 (d, J=243.9 Hz, Ar-p); 178.1 (COOH).

TLC data: solvent: EA; R$_F$=0.35

Melting point: 73° C.

c) Synthesis of (S)-4-fluorophenyl lactate (S)-3

Reaction mixture: 452 mg (2.5 mmol) (S)-4-fluorophenylalanine, 750 mg (10.9 mmol) of NaNO$_2$ in 5.4 ml H$_2$SO$_4$ (1M).

Yield: 330 mg (72.5%), white crystals $^1$H NMR: see rac-4-fluorophenyl lactate $^{13}$C NMR: see rac-4-fluorophenyl lactate TLC data: solvent: EA, R$_F$=0.35

Melting point 69° C.

The compounds (S)-(+)-2-hydroxy-3-methylbutanoic acid (S)-(−)-2-hydroxy-4-methylpentanoic acid (S)-2-hydroxy-4-phenylbutyric acid (S)-2-hydroxy-3-phenylpropanoic acid were synthesized analogously to Example 1, starting from the corresponding commercially available enantiomerically pure amino acids.

EXAMPLE 2

Screening for Racemase Activity

To obtain a first indication regarding the racemization activity of the microorganisms, they were observed for racemization of the (natural) substrate (S)-lactate 1 and/or the (non-natural) substrates (S)-phenyl lactate 2 and (S)-4-fluorophenyl lactate 3.

For the screening, approximately 10 mg of lyophilized cells were rehydrated in an Eppendorf vial in 900 μl of Bis-Tris buffer (50 mM Bis-Tris, pH=6) for one hour at 42° C. and 150 rpm. Then, in each case 10 mg substrate which had previously been dissolved in 100 μl of buffer and brought to pH 6-7 with NaOH were added. The reaction mixtures were incubated in a shaker-incubator at 42° C. and 150 rpm. A blank value, where identical reaction conditions were maintained without addition of cells, was measured in parallel with each reaction mixture. Since all the control experiments were negative, spontaneous racemization under the given reaction conditions can be ruled out.

After one or two days in the shaker-incubator, the Eppendorf vials were centrifuged for 5 minutes at 13000 rmp and in each case 400 μl of the supernatant solution were subsequently removed. The solution was extracted twice by shaking with in each case 600 μl of EA and the organic phases were combined and dried over Na$_2$SO$_4$, and the solvent was evaporated on a rotary evaporator. To achieve separation of the two enantiomers with a chiral column, all of the compounds studied required derivatization. To this end, each sample was treated with 500 μl of BF$_3$-methanol, shaken for 10 minutes at 60° C. and extracted by shaking with 1 ml of CH$_2$Cl$_2$. The organic phase was dried over Na$_2$SO$_4$ and concentrated to a volume of approximately 100 μl.

A racemization reaction was considered negative (−) when the enantiomeric excess after 2 days amounted to >95%; enantiomeric excesses of <20% were assessed as positive (+). Any other result received the score (~). The results of the screenings are compiled in Table 6.

TABLE 6

Results of the activity screening

| Microorganism | DSM Number | Substrate (S)-1 | (S)-2 | (S)-3 |
|---|---|---|---|---|
| L. paracasei | 20008 | + | + | + |
| L. paracasei | 20207 | + | + | + |
| L. paracasei | 2649 | − | + | + |
| L. acidophilus | 20079 | n.d. | − | − |
| L. brevis | 20054 | + | − | − |
| L. piscicola (L. carnis) | 20722 | n.d. | − | − |
| L. halotolerans | 20190 | + | − | − |
| L. confusus | 20196 | − | − | − |
| L. acetotolerans | 20749 | + | ~ | − |
| L. delbrueckii | 20074 | + | + | + |
| L. kandleri | 20593 | n.b. | − | − |
| L. fructosus | 20349 | − | − | − |
| L. farciminis | 20184 | − | ~ | − |
| L. gasseri | 20243 | n.d. | − | − |
| L. alimentarius | 20249 | + | − | − |
| L. jensenii | 20557 | + | − | − |
| L. halofax volcanii | 5176 | n.d. | − | − |
| L. haloarcula vallismortis | 3756 | n.d. | − | − |

+= good activity
−= no activity
~= moderate activity
n.d.= not determined

EXAMPLE 3

Determination of the Enantiomeric Excesses with Various Substrates

For determining the enantiomeric excesses, the procedure of Example 2 was followed, except that the amount of cells employed was reduced to 50 mg.

a) Experiments with L-(−)-3-phenyllactic acid as Substrate

First, 50 mg of lyophilized cells were treated with 1 ml of Bis-Tris buffer (50 mM, pH6) and rehydrated for 1 hour in a shaker-incubator at 42° C. and 150 rpm. Thereafter, in each case 5 mg of substrate, dissolved in 100 μl of buffer, were added and the mixtures were incubated in a shaker-incubator (30° C., 150 rpm). All samples were measured by means of chiral GC after in each case 24, or 48, hours. To achieve separation of the enantiomers by GC, the samples required derivatization.

The derivatization was carried out with BF$_3$-methanol (see above) or with trifluoroacetic anhydride. For the derivatization with trifluoroacetic anhydride, 5 mg of 3-phenyllactic acid were dissolved in 500 μl of CH$_2$Cl$_2$, treated with 5 drops of trifluoroacetic anhydride, shaken for 1 minute at room temperature and subsequently treated with approximately 500 μl of $H_2O$. The organic phase is dried over $Na_2SO_4$, and the samples were then measured by GC on a chiral column.

The results were calculated using the following formulae:

ee[%]:(R−S)/(R+S)×100 conversion rate[%]:R/(R+S)×100 racemization[%]:2R/(R+S)×100

In addition to the strain *Lactobacillus paracasei* subsp. *paracasei* DSM 20008, the following four further strains with good or excellent racemase activity with regard to L-(−)-3-phenyllactic acid were found:
  *Lactobacillus paracasei* subsp. *paracasei* DSM 2649
  *Lactobacillus paracasei* subsp. *paracasei* DSM 20207
  *Lactobacillus delbrueckii* subsp. *delbrueckii* DSM 2649
  *Lactobacillus oris* DSM 4864

The results for the above strains are compiled in Table 7 and shown as culture condition groups (shaker or drying oven; argon or natural atmosphere) and culture time groups.

The two substrates were reacted with all the strains. The degree of racemization was measured by GC after in each case 24 hours and 48 hours.

In the case of (S)-(+)-2-hydroxy-3-methylbutanoic acid, only strain DSM 20207 reveals activity. A total of 5 strains revealed racemization toward the substrate (S)-(−)-2-hydroxyisocaproic acid. The results are compiled in Tables 8 and 9.

TABLE 8

Screening with (S)-(+)-2-hydroxy-3-methylbutanoic acid

| Strain | 24 hours | | | 48 hours | | |
|---|---|---|---|---|---|---|
| | ee [%] | conv. rate [%] | racem. [%] | ee [%] | conv. rate [%] | racem. [%] |
| DSM 20207 | 86 | 7 | 14 | 73 | 14 | 27 |

TABLE 7

Results of the screening with L(−)-phenyllactic acid

| DSM | | Drying oven (argon) | | | | | | Shaker (air) | | |
|---|---|---|---|---|---|---|---|---|---|---|
| | | 24 h | | | 48 h | | | 24 h | | |
| number of the strain | harvest on day | ee [%] | conv. rate [%] | racem. [%] | ee [%] | conv. rate [%] | racem. [%] | ee [%] | conv. rate [%] | racem. [%] |
| 2649 | 3 | 80 | 10 | 20 | 49 | 26 | 51 | 69 | 15 | 31 |
| | 4 | 14 | 43 | 86 | 0 | 50 | 100 | | | |
| 20207 | 3 | 8 | 46 | 92 | 0 | 50 | 100 | | | |
| | 4 | | | | | | | 65 | 17 | 35 |
| 20074 | 3 | 83 | 8 | 16 | 64 | 18 | 36 | — | — | — |
| 4864 | 4 | | | | | | | 23 | 38 | 77 |
| 20008 | 3 | 0 | 50 | 100 | 0 | 50 | 100 | | | |

| DSM | | Shaker (air) | | | Drying oven (ar) | | | | | |
|---|---|---|---|---|---|---|---|---|---|---|
| | | 48 h | | | 24 h | | | 48 h | | |
| number of the strain | harvest on day | ee [%] | conv. rate [%] | racem. [%] | ee [%] | conv. rate [%] | racem. [%] | ee [%] | conv. rate [%] | racem. [%] |
| 2649 | 3 | 51 | 24 | 49 | 77 | 12 | 23 | 0 | 50 | 100 |
| | 4 | | | | | | | | | |
| 20207 | 3 | | | | | | | | | |
| | 4 | 46 | 26 | 54 | 17 | 41 | 83 | 0 | 50 | 100 |
| 20074 | 3 | — | — | — | 13 | 43 | 87 | 0 | 50 | 100 |
| 4864 | 4 | 0 | 50 | 100 | 70 | 15 | 30 | 45 | 27 | 55 |
| 20008 | 3 | | | | 0 | 50 | 100 | 0 | 50 | 100 |

To determine whether the racemase activity observed correlates with a lactate racemase activity, the natural substrate L-(+)-lactic acid was reacted with the strains which revealed good to very good activity with L-(−)-3-phenyllactic acid.

It emerged that 100% racemization was detectable after as little as 24 hours when the strains DSM 20207, 20074 and 20008 were allowed to convert the natural substrate L-(+)-lactic acid.

No conversion was obtained with strain DSM 2649.

b) Experiments with Various Other Alkyl Substrates

The following were used as substrates:
  (S)-(+)-2-hydroxy-3-methylbutanoic acid ($C_5H_{10}O_3$)
  (S)-(−)-2-hydroxyisocaproic acid ($C_6H_{12}O_3$)

TABLE 9

Screening with (S)-(−)-2-hydroxyisocaproic acid

| Strain | 24 hours | | | 48 hours | | |
|---|---|---|---|---|---|---|
| | ee [%] | conv. rate [%] | racem. [%] | ee [%] | conv. rate [%] | racem. [%] |
| DSM 2649 | 88 | 6 | 12 | 75 | 12 | 25 |
| DSM 20008 | 85 | 7 | 15 | 82 | 9 | 18 |
| DSM 20207 | 94 | 3 | 6 | 73 | 14 | 17 |
| DSM 20074 | 94 | 3 | 6 | 93 | 4 | 7 |

TABLE 9-continued

Screening with (S)-(−)-2-hydroxyisocaproic acid

| | 24 hours | | | 48 hours | | |
|---|---|---|---|---|---|---|
| Strain | ee [%] | conv. rate [%] | racem. [%] | ee [%] | conv. rate [%] | racem. [%] |
| DSM 20017 | 86 | 7 | 14 | 89 | 10 | 20 |

In summary, it can be stated that, again, the same strains which had been active toward L-(−)-3-phenyllactic acid also revealed an activity here.

c) Experiments with (S)-2-hydroxy-4-phenylbutyric acid

The degree of racemization was measured by HPLC after in each case 24 hours and 48 hours. The results are compiled in Table 10.

TABLE 10

Screening with (S)-2-hydroxy-4-phenylbutyric acid

| | 24 hours | | |
|---|---|---|---|
| Strain | ee [%] | conv. rate [%] | racem. [%] |
| DSM 2649 | 6 | 47 | 94 |
| DSM 20054 | 90 | 5 | 10 |
| DSM 20190 | 70 | 15 | 30 |
| DSM 20008 | 25 | 38 | 75 |
| DSM 20207 | 3 | 48 | 97 |
| DSM 20749 | 48 | 26 | 52 |

In connection with the present invention, the following microorganisms of the DSMZ, which are available to the public, were redeposited on 11 Jul. 2003 in accordance with the rules of the Budapest Treaty with DSMZ (Deutsche Sammlung von Mikroorganismen und Zellkulturen GmbH; German Collection of Microorganisms and Cell Cultures, Inhoffenstraβe 7 B, 38124 Braunschweig, Germany).

| DSM Number | Deposit Number |
|---|---|
| 20207 | DSM 15755 |
| 20074 | DSM 15754 |
| 20017 | DSM 15753 |
| 4864 | DSM 15752 |
| 2649 | DSM 15751 |

We claim:

1. A method for the microbiological isomerization of alpha-hydroxycarboxylic acids of the formula I

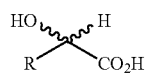

where
R is straight-chain or branched $C_2$-$C_8$ alkyl or $C_2$-$C_8$ alkenyl or —$(CH_2)_n$-Cyc, where n is an integer of 0 to 4, and Cyc is an unsubstituted or mono- or polysubstituted, mono- or binuclear carbo- or heterocyclic ring,
wherein said method comprises isomerizing a substrate consisting essentially of a first stereoisomer of an alpha-hydroxycarboxylic acid of the formula (I) with an enzyme in a reaction medium to obtain a second stereoisomer or an isomer mixture comprising the first stereoisomer and the second stereoisomer,
wherein the enzyme is contained in an extract of a microorganism or present in intact cells of a microorganism which express the enzyme, wherein said microorganism is selected from the group consisting of the strains *L. paracasei* DSM 15755, *L. paracasei* DSM 15751, *L. delbrueckii* DSM 15754, *L. sakei* DSM 15753 and *L. oris* DSM 15752, and wherein said microorganism is capable of racemizing at least one compound selected from the group consisting of (R) and/or (S) form of phenyl lactate, 4-fluorophenyl lactate, 2-hydroxy-4-phenylbutyric acid, 2-hydroxy-4-methylpentanecarboxylic acid and 2-hydroxy-3-methylbutyric acid.

2. The method of claim 1, wherein the second stereoisomer is removed from the isomer mixture and the remaining part of the isomer mixture is subjected to a further isomerization step.

3. The method of claim 1, wherein the isomer mixture is subjected to a subsequent chemical or enzymatic stereoselective reaction and a reaction mixture is obtained, wherein the reaction mixture obtained is subjected to a further isomerization step.

4. The method of claim 1, wherein the isomerization reaction is coupled with a subsequent chemical or enzymatic, enantioselective reaction, during which the second stereoisomer is removed from the reaction medium.

5. The method of claim 3, wherein the subsequent chemical or enzymatic, enantioselective reaction is an esterification or an amidation of the alpha-hydroxycarboxylic acid.

6. A method for the microbiological isomerization of alpha-hydroxycarboxylic acids of the formula I

where
R is straight-chain or branched $C_2$-$C_8$ alkyl or $C_2$-$C_8$ alkenyl or —$(CH_2)_n$-Cyc, where n is an integer of 0 to 4, and Cyc is an unsubstituted or mono- or polysubstituted, mono- or binuclear carbo- or heterocyclic ring,
wherein said method comprises
(i) screening and obtaining a microorganism of the genus *Lactobacillus* that is capable of racemizing at least one compound selected from the group consisting of (R) and/or (S) form of phenyl lactate, 4-fluorophenyl lactate, 2-hydroxy-4-phenylbutyric acid, 2-hydroxy-4-methylpentanecarboxylic acid and 2-hydroxy-3-methylbutyric acid,
(ii) isomerizing a substrate consisting essentially of a first stereoisomer of an alpha-hydroxycarboxylic acid of the formula (I) with an enzyme in a reaction medium to obtain a second stereoisomer or an isomer mixture comprising the first stereoisomer and the second stereoisomer, wherein the enzyme is contained in an extract of said microorganism or present in intact cells of said microorganism which express the enzyme, wherein said microorganism is selected from the group consisting of the strains *L. paracasei* DSM 15755, *L. paracasei* DSM 15751, *L. delbrueckii* DSM 15754, *L. sakei* DSM 15753 and *L. oris* DSM 15752.

7. The method of claim 6, wherein the second stereoisomer is removed from the isomer mixture and the remaining part of the isomer mixture is subjected to a further isomerization step.

8. The method of claim 6, wherein the isomer mixture is subjected to a subsequent chemical or enzymatic stereoselective reaction and a reaction mixture is obtained, wherein the reaction mixture obtained is subjected to a further isomerization step.

9. The method of claim 6, wherein the isomerization reaction is coupled with a subsequent chemical or enzymatic, enantioselective reaction, during which the second stereoisomer is removed from the reaction medium.

10. The method of claim 8, wherein the subsequent chemical or enzymatic, enantioselective reaction is an esterification or an amidation of the alpha-hydroxycarboxylic acid.

* * * * *